United States Patent
Hong et al.

(10) Patent No.: US 12,332,200 B2
(45) Date of Patent: Jun. 17, 2025

(54) APPARATUS AND METHOD WITH ELECTRODE-BASED MEASUREMENT

(71) Applicant: SAMSUNG ELECTRONICS CO., LTD., Suwon-si (KR)

(72) Inventors: Hyeokki Hong, Suwon-si (KR); Chisung Bae, Suwon-si (KR); Kitae Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 162 days.

(21) Appl. No.: 18/176,183

(22) Filed: Feb. 28, 2023

(65) Prior Publication Data
US 2024/0077440 A1    Mar. 7, 2024

(30) Foreign Application Priority Data
Sep. 2, 2022    (KR) .................. 10-2022-0111531

(51) Int. Cl.
| | | |
|---|---|---|
| G01N 27/00 | (2006.01) | |
| G01N 33/483 | (2006.01) | |
| G06F 11/16 | (2006.01) | |

(52) U.S. Cl.
CPC ......... *G01N 27/00* (2013.01); *G01N 33/4836* (2013.01); *G06F 11/1675* (2013.01)

(58) Field of Classification Search
CPC .. G01N 27/00; G01N 33/4836; G06F 11/008; G06F 11/1675
See application file for complete search history.

(56) References Cited

U.S. PATENT DOCUMENTS

| | | |
|---|---|---|
| 4,201,976 A | 5/1980 | Patel |
| 4,205,324 A | 5/1980 | Patel |
| 6,924,755 B1 | 8/2005 | Callanan et al. |
| 7,896,807 B2 | 3/2011 | Clancy et al. |
| 7,944,383 B2 | 5/2011 | Doris |
| 8,473,669 B2 | 6/2013 | Sinclair |

(Continued)

FOREIGN PATENT DOCUMENTS

KR    10-2375088 B1    3/2022

OTHER PUBLICATIONS

Extended European Search Report Issued on Jan. 23, 2024, in Counterpart European Patent Application No. 23194876.1 (8 Pages in English).

(Continued)

*Primary Examiner* — Neel D Shah
*Assistant Examiner* — Adam S Clarke
(74) *Attorney, Agent, or Firm* — NSIP Law

(57) ABSTRACT

A measuring apparatus implementing an electrode array and an operating method of the measuring apparatus are provided. The measuring apparatus may include an electrode array configured to measure input signals of an analog domain through electrodes arranged in a target point, main signal processors configured to perform signal processing operations including a digital conversion operation of corresponding input signals of the input signals, respectively, and auxiliary signal processors configured to replace at least one of the main signal processors, and perform at least some of the signal processing operations including the digital conversion operation in response to a replacement condition being satisfied.

20 Claims, 11 Drawing Sheets

(56) References Cited

U.S. PATENT DOCUMENTS

| | | | |
|---|---|---|---|
| 8,884,629 | B1 | 11/2014 | Kumar et al. |
| 9,007,243 | B2 | 4/2015 | Kappes |
| 11,177,822 | B2 | 11/2021 | Singh et al. |
| 2013/0338473 | A1 | 12/2013 | Bohorquez et al. |
| 2015/0269038 | A1* | 9/2015 | Perez ............. G06F 11/2033 714/5.1 |
| 2018/0349235 | A1 | 12/2018 | Freydel et al. |
| 2021/0313987 | A1* | 10/2021 | Faldu ............. A61N 1/05 |

OTHER PUBLICATIONS

J. Drags, et al., "In Vitro Multi-Functional Microelectrode Array Featuring 59 760 Electrodes, 2048 Electrophysiology Channels, Stimulation, Impedance Measurement, and Neurotransmitter Detection Channels" *IEEE journal of solid-state circuits* vol. 52 No. 6, Jun. 2017 (pp. 1576-1590).

J. Abbott, et al., "A nanoelectrode array for obtaining intracellular recordings from thousands of connected neurons" *Nature biomedical engineering* vol. 4 No. 2, Feb. 2020 (pp. 232-241).

J. Abbott, et al., "The Design of a CMOS Nanoelectrode Array With 4096 Current-Clamp/Voltage-Clamp Amplifiers for Intracellular Recording/Stimulation of Mammalian Neurons" *IEEE journal of solid-state circuits* vol. 55 No. 9, Sep. 2020 (pp. 2567-2582).

D. Wendler, et al., "28.7 A 0.00378mm2 Scalable Neural Recording Front-End for Fully Immersible Neural Probes Based on a Two-Step Incremental Delta-Sigma Converter with Extended Counting and Hardware Reuse" *2021 IEEE International Solid-State Circuits Conference (ISSCC)*. vol. 64. IEEE, Mar. 3, 2021 (pp. 398-400).

Han-Sol Lee, et al., "High-density neural recording system design" *Biomedical Engineering Letters* vol. 12 No. 3, May 30, 2022 (pp. 1-11).

\* cited by examiner

APPARATUS AND METHOD WITH ELECTRODE-BASED MEASUREMENT

CROSS-REFERENCE TO RELATED APPLICATIONS

This application claims the benefit under 35 USC § 119(a) of Korean Patent Application No. 10-2022-0111531 filed on Sep. 2, 2022, in the Korean Intellectual Property Office, the entire disclosure of which is incorporated herein by reference for all purposes.

BACKGROUND

1. Field

The following description relates to an apparatus and method with electrode-based measurement.

2. Description of Related Art

Biosignals may be signals from plants or animals, for example, that can be continually measured and monitored. A biosignal measuring technique may measure a biosignal from a living body through a medium, such as an electrode array. A measuring device including an electrode array may be inserted into or attached to a living body, and may collect or receive a biosignal. In an example, the biosignal may include a neural signal, a brainwave signal, a muscle signal, and the like.

SUMMARY

This Summary is provided to introduce a selection of concepts in a simplified form that is further described below in the Detailed Description. This Summary is not intended to identify key features or essential features of the claimed subject matter, nor is it intended to be used as an aid in determining the scope of the claimed subject matter.

In a general aspect, an apparatus includes an electrode array configured to measure input signals of an analog domain through electrodes arranged in a target point; main signal processors configured to perform signal processing operations on corresponding respective input signals of the input signals; and auxiliary signal processors configured to replace at least one of the main signal processors, and perform at least some of the signal processing operations in response to a replacement condition being satisfied.

The signal processing operations may include at least one of a digital conversion operation, a signal generation operation, a signal amplification operation, a control operation, and a clock generation operation.

The apparatus may include multiplexers (MUXs) configured to selectively connect candidate electrodes of the electrodes to corresponding auxiliary signal processors of the auxiliary signal processors.

The main signal processors may include a first main signal processor connected to a first electrode of the electrodes, the MUXs may include a first MUX configured to selectively connect a first auxiliary signal processor of the auxiliary signal processors to first candidate electrodes comprising the first electrode, and the first MUX may be configured to connect the first electrode to the first auxiliary signal processor in response to the replacement condition being satisfied by the first main signal processor.

Each of the main signal processors may include an analog digital converter (ADC) configured to perform the digital conversion operation.

The main signal processors may be connected to the respective electrodes before the replacement condition is satisfied.

The main signal processors may be divided into a predetermined first number of main signal processors, and configure a plurality of slots, and the auxiliary signal processors may be divided into a predetermined second number of auxiliary signal processors, and are dedicatedly allocated to each of the plurality of slots.

The main signal processors may be divided into a predetermined first number, and configure a plurality of slots, and the auxiliary signal processors may be allocated to the plurality of slots such that a predetermined third number of slots of the plurality of slots share at least a portion of the auxiliary signal processors.

The apparatus may include a controller configured to determine whether the main signal processors satisfy the replacement condition based on a performance test of the main signal processors.

The controller is configured to, while connection between the electrodes and the main signal processors is open, provide a test signal to each of the main signal processors, analyze a processing result of each of the main signal processors in response to the test signal, and determine whether the main signal processors satisfy the replacement condition.

The controller may be configured to, when a plurality of replacement targets satisfying the replacement condition is detected from the main signal processors, determine a replacement priority of the replacement targets based on a defect level of the replacement targets and apply the auxiliary signal processor in an order from a highest priority to a lowest priority.

The electrodes may include main electrodes connected to the main signal processors and auxiliary electrodes connected to the auxiliary signal processors, and the electrode array may be configured to measure the input signals by implementing the main electrodes and the auxiliary electrodes.

The main signal processors may include a first main signal processor connected to a first main electrode among the main electrodes, the auxiliary signal processors comprise a first auxiliary signal processor connected to a first auxiliary electrode among the auxiliary electrodes, and the first auxiliary signal processor is configured to replace the first main signal processor and connect to the first main electrode in response to the replacement condition being satisfied by the first main signal processor.

The main electrodes may be arranged in a central area of the electrode array compared to the auxiliary electrodes, and data measurement through the first auxiliary electrode may b paused in response to the replacement condition being satisfied by the first main signal processor.

The main signal processors may include first main signal processors selectively connected to each electrode of a first electrode group among the electrodes, the auxiliary signal processors may include first auxiliary signal processors selectively connected to each electrode of the first electrode group, and some of the first main signal processors and the first auxiliary signal processors selected in order from a high performance level to a low performance level may be applied to the first electrode group.

The electrode array may include a multi-channel microelectrode array (MEA).

In a general aspect, a method includes measuring input signals of an analog domain through electrodes of an electrode array arranged in a target point; performing signal processing operations on corresponding respective input signals of the input signals by implementing respective main signal processors; and performing at least some of the signal processing operations by implementing auxiliary signal processors instead of the main signal processors in response to a replacement condition being satisfied.

The signal processing operations may include at least one of a digital conversion operation, a signal generation operation, a signal amplification operation, a control operation, and a clock generation operation.

The performing of the at least some of the signal processing operations by implementing the auxiliary signal processors may include implementing the auxiliary signal processors instead of the main signal processors with multiplexers (MUXs) that are configured to selectively connect candidate electrodes of the electrodes to corresponding auxiliary signal processors of the auxiliary signal processors.

The main signal processors may be divided into a predetermined first number of main signal processors and configure a plurality of slots, and the auxiliary signal processors may be divided into a predetermined second number of auxiliary signal processors and are dedicatedly allocated to each of the plurality of slots.

The electrode array may include a multi-channel microelectrode array (MEA).

In a general aspect, an apparatus includes a measuring apparatus including an electrode array configured to generate input signals corresponding to data that is measured from target points by electrodes arranged in the target points, main signal processors configured to perform signal processing operations on respective corresponding input signals of the input signals, and auxiliary signal processors configured to replace the main signal processors and perform at least some of the signal processing operations in response to a replacement condition being satisfied; and a memory configured to store response data output by at least some of the main signal processors and the auxiliary signal processors, wherein the signal processing operations comprise a digital conversion operation.

An apparatus, an electrode array comprising a plurality of electrodes disposed on target points; analog to digital converters (ADC) configured to perform respective digital conversion operations on input signals of respective signal transmission channels; respective auxiliary signal processors configured to perform one or more channel exchanges to replace a corresponding one or more of respective digital conversion operations of one or more of the ADCs based on a determination of a defect in the one or more ADCs; and a multiplexer (MUX) configured to selectively perform connection operations between one or more electrodes of the electrode array and a corresponding one or more of the auxiliary signal processors of the respective auxiliary signal processors.

The electrode array may be a multi-channel microelectrode array (MEA).

The MUX is configured to select which connection operations to perform based on the determination of the defect in the one or more of the ADCs.

Other features and aspects will be apparent from the following detailed description, the drawings, and the claims.

Figure 1:
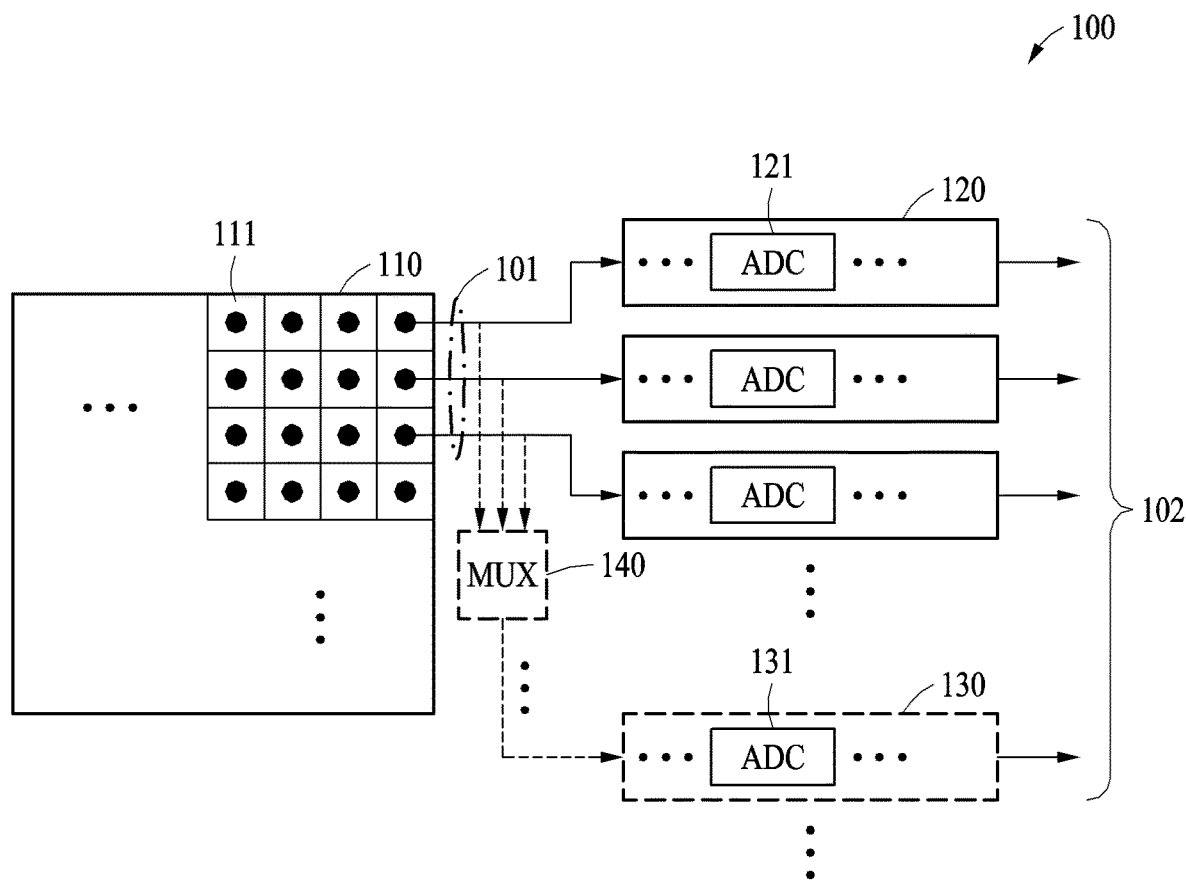
FIG. 1 illustrates an example schematic structure of an example measuring apparatus, in accordance with one or more embodiments.

Throughout the drawings and the detailed description, unless otherwise described or provided, the same or like drawing reference numerals may be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known, after an understanding of the disclosure of this application, may be omitted for increased clarity and conciseness, noting that omissions of features and their descriptions are also not intended to be admissions of their general knowledge.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

The terminology used herein is for the purpose of describing particular examples only, and is not to be used to limit the disclosure. As used herein, the singular forms "a," "an," and "the" are intended to include the plural forms as well, unless the context clearly indicates otherwise. As used herein, the term "and/or" includes any one and any combination of any two or more of the associated listed items. As used herein, the terms "include," "comprise," and "have" specify the presence of stated features, numbers, operations, elements, components, and/or combinations thereof, but do not preclude the presence or addition of one or more other features, numbers, operations, elements, components, and/or combinations thereof. The use of the term "may" herein with respect to an example or embodiment (for example, as to what an example or embodiment may include or implement) means that at least one example or embodiment exists where such a feature is included or implemented, while all examples are not limited thereto.

As used herein, for phrases "at least one of A and B", "at least one of A, B, or C," and the like, each list may include any one of the listed items in the corresponding one of the phrases, or all possible combinations thereof.

Unless otherwise defined, all terms including technical and scientific terms, used herein have the same meaning as commonly understood by one of ordinary skill in the art to which this disclosure pertains consistent with and after an understanding of the present disclosure. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

FIG. 1 illustrates an example schematic structure of an example measuring apparatus, in accordance with one or more embodiments. Referring to FIG. 1, a measuring apparatus 100 may include an electrode array 110. For example, the electrode array 110 may be, as an example, a multi-channel microelectrode array (MEA). The electrode array 110 may include a plurality of electrodes, such as an electrode 111. The plurality of electrodes may be arranged or disposed on target points, and input signals 101 of an analog domain may be measured through the plurality of electrodes. As an example, the target points may be a living body including some or all parts of various living organisms, such as, but not limited to, a human body, an animal, a plant, and the like. In an example, the targets may be neurons or nerve cells. The electrodes may include a metal material and may contact a target point. The input signal may be measured by each electrode and the number of input signals 101 may be the same as the number of electrodes.

The measuring apparatus 100 may include a plurality of main signal processors, such as a main signal processor 120. In an example, the main signal processor 120 may correspond to an analog front end (AFE). Each of the main signal processors may perform signal processing operations on a corresponding input signal among the input signals 101. Each of the main signal processors may configure each signal transmission channel. Each corresponding input signal may have a corresponding relationship with each of the main signal processors. For example, when the input signals 101 include a first input signal, a second input signal, and a third input signal, and the plurality of main signal processors include a first main signal processor configured to receive the first input signal, a second main signal processor configured to receive the second input signal, a third main signal processor configured to receive the third input signal, the first main signal processor and the first input signal, the second main signal processor and the second input signal, and the third main signal processor and the third input signal may have corresponding relationships, respectively.

According to one embodiment, signal processing may include a digital conversion operation. In implementing the digital conversion operation, an input signal may be converted from an analog domain to a digital domain. Each of the main signal processors may include an analog to digital converter (ADC), and may perform a digital conversion operation on the corresponding input signal using the ADC. According to one embodiment, signal processing may include various operations that are performed through various components. For example, signal processing may include a signal generation operation using a signal generator (e.g., a current generator, a voltage generator, etc.), a signal amplification operation using an amplifier, a control operation using a controller, and a clock generation operation using a clock generator. The signal generator and the amplifier may be included in the analog domain, and the controller and the clock generator may be included in the digital domain. The analog domain and the digital domain may be distinguished by the ADC.

The measuring apparatus 100 may include a plurality of auxiliary signal processors, such as an auxiliary signal processor 130. In an example, if an error condition or defect occurs in one or more of the main signal processors 120, the one or more main signal processors 120 in which the error condition or defect occurs may be replaced by corresponding one or more of the auxiliary signal processors 130. The one or more main signal processors 120 may be replaced by the one or more auxiliary signal processors 130 if a replacement condition, for example, a defect in the one or more main signal processors 120, is met or satisfied.

A determination of whether a replacement condition has been satisfied may be obtained after the respective main signal processors are connected to the electrodes 111. In response to the replacement condition of the main signal processors 120 being satisfied, the auxiliary signal processor 130 may at least partially replace the main signal processor 120, and may perform the same or similar signal processing operations that the main signal processor 120 performs.

In a non-limiting example, the replacement condition may include an occurrence of a defect in at least a portion of signal processing of the main signal processor 120. For example, the defect may include an error or a performance degradation. Performance degradation may be regarded as a more severe defect than the occurrence of an error. For example, when an error occurs in the ADC of the main signal processor 120, or the performance of the ADC of the main signal processor 120 degrades, the occurrence of the error or the occurrence of the performance degradation of the ADC in the main signal processor 120 may satisfy the replacement condition. In this example, the auxiliary signal processor 130 may at least partially replace signal processing operations of the main signal processor 120. As a non-limited example, the auxiliary signal processor 130 may replace the entire signal processing operations of the main signal processor 120, or alternately, may replace an ADC process in the signal processing operations of the main signal processor 120. The replacement of the main signal processor 120 by the auxiliary signal processor 130 may be referred to as channel exchange.

The measuring apparatus 100 may include a plurality of multiplexers (MUX), such as a MUX 140. In a non-limited example, the number of MUXs 140 may be the same as the number of auxiliary signal processors 130. However, this is only an example, and the number of MUXs 140 may be different from the number of auxiliary signal processors 130. A MUX 140 may provide a signal path that is used by an auxiliary signal processor 130 to replace a main signal processor 120. The size of the MUX 140 may depend on the number of electrodes covered by the MUX 140 and/or the number of main signal processors 120. For example, as illustrated in FIG. 1, when the MUX 140 covers or controls three electrodes and/or three signal processors, the MUX 140 may have a size corresponding to the number of covered electrodes and/or signal processors.

The electrodes that are covered or controlled by the MUX 140 may be referred to as candidate electrodes. In a non-limited example, each MUX 140 may correspond to each auxiliary signal processor 130. Each MUX 140 may selectively connect each candidate electrode 111 to a corresponding auxiliary signal processor 130. Selective connection may represent a state that may open or close through a circuit control (e.g., switching). For example, when the main signal processor 120 is connected to a first electrode 111, the MUX 140 may selectively connect candidate electrodes 111 including the first electrode to the auxiliary signal processor 130. In this example, in response to the main signal processor 120 that satisfies the replacement condition, the MUX 140 may connect the first electrode 111 to the auxiliary signal processor 130.

The number of connectable input signals of the auxiliary signal processor 130 may vary based on the size of the MUX 140, and by adjusting the size of the MUX 140, and through this process, a coverable range of the auxiliary signal processor 130 and a complexity of the MUX 140 may be determined. The main signal processors 120 and the auxiliary signal processors 130 may produce output signals 102 based on input signals 101. The output signal(s) 102 may include a measurement result of a target point. For example, the output signal(s) 102 may include a bioreaction or a biological (or biosignal), such as a neural signal, a brainwave signal, a muscle signal, a temperature, and a location. In an example, the output signal may refer to a change in current produced by the sum of an electrical potential difference across a specialized tissue, organ or cell system of a living organism.

According to one embodiment, electrodes of the electrode array 110 may form high-density multi-channels. In a non-limited example, the number of channels may be more than 10K. Additionally, the electrode array 110 may be implemented by a single chip (e.g., a biochip). In this example, when producing a high-density multi-channel single chip, it may be difficult to apply a process of selecting a good die. This characteristic may significantly decrease a production yield rate. Additionally, electrodes in the electrode array 110 may need to be utilized as much as possible. However, when the measuring apparatus 100 is inserted into a body, it may be difficult to remove the measuring apparatus 100 from the body and repair the measuring apparatus 100 even though a problem has occurred in the measuring apparatus 100.

Even if a problem occurs due to a defect in some channels of the measuring apparatus 100 when the measuring apparatus 100 is implemented, the problems related to the defective channels may be solved by the implementation of an auxiliary signal processor, and thus, the production yield rate of the measuring apparatus 100 may improve and the usage period of the measuring apparatus 100 may be extended. Additionally, the auxiliary signal processor 130 may increase, maximize and/or optimize the performance of the measuring apparatus 100.

Figure 2:
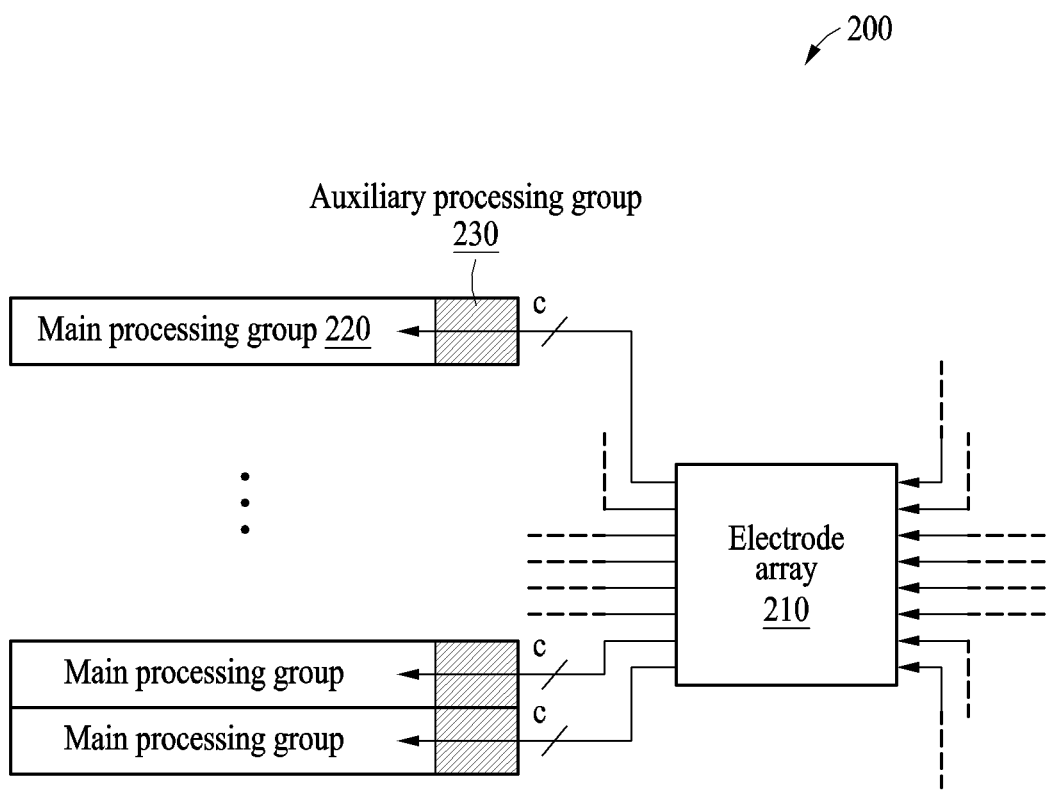
FIG. 2 illustrates an example configuration of a slot of an example measuring apparatus, in accordance with one or more embodiments.

FIG. 2 is a diagram illustrating an example configuration of a slot of an example measuring apparatus, in accordance with one or more embodiments.

Referring to FIG. 2, an example measuring apparatus 200 may include an electrode array 210, main processing groups, such as a main processing group 220, and auxiliary processing groups, such as an auxiliary processing group 230. Each main processing group may include a plurality of main signal processors, and each auxiliary processing group 230 may include a plurality of auxiliary signal processors.

In an example, each main processing group may configure one slot. In an example, the main signal processors may be divided into a predetermined first number, and may configure a plurality of slots and the auxiliary signal processors may be divided into a predetermined second number and may be allocated to each of the plurality of slots.

Figure 7:
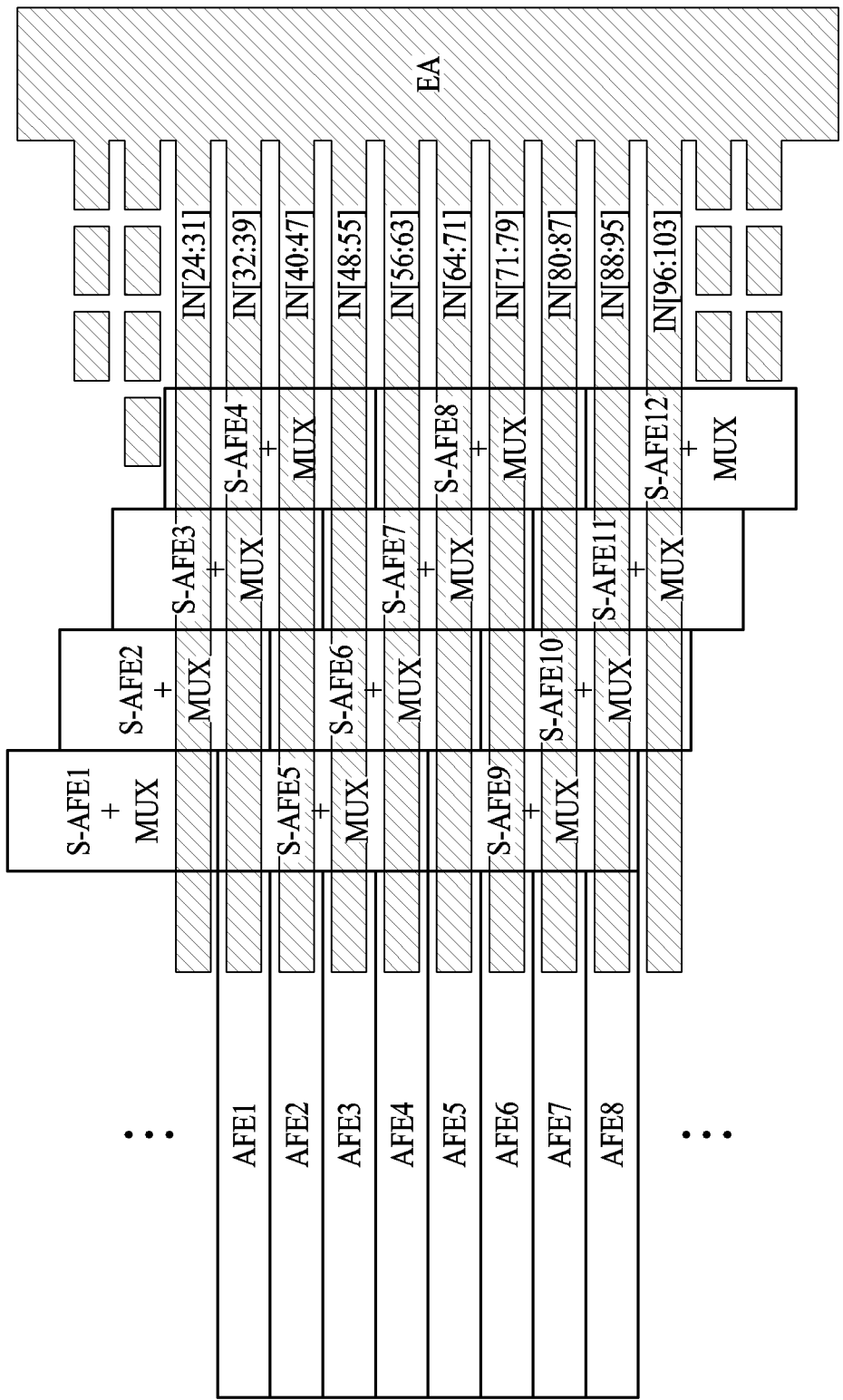
FIG. 7 illustrates an example relationship between components in a structure in which auxiliary signal processors are shared, in accordance with one or more embodiments.
Figure 8:
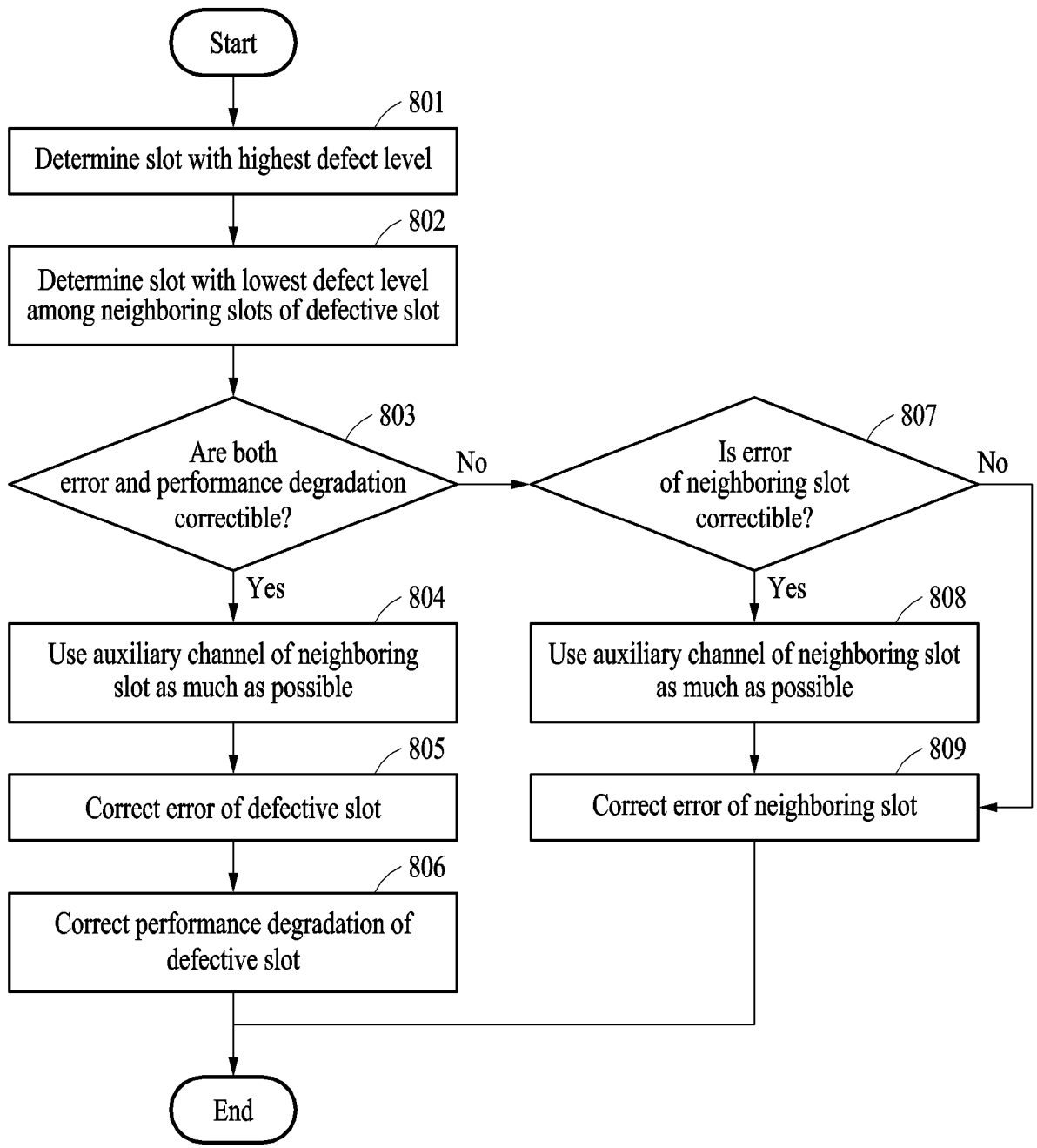
FIG. 8 is a flowchart illustrating an example optimization operation of channel exchange, in accordance with one or more embodiments.

Referring to FIG. 2, c may denote the predetermined first number of main signal processors. For example, the predetermined first number of main signal processors may be 32 and the second number may be 4. In this example, 32 main signal processors may configure one slot and for each slot, 4 auxiliary signal processors may be allocated. In this example, each slot may process 32 channels. Referring to an example illustrated in FIG. 2, the second number of auxiliary signal processors may be dedicatedly allocated to each slot. However, as illustrated in FIGS. 7 and 8, main signal processors in different slots may share any auxiliary signal processors.

Figure 3:
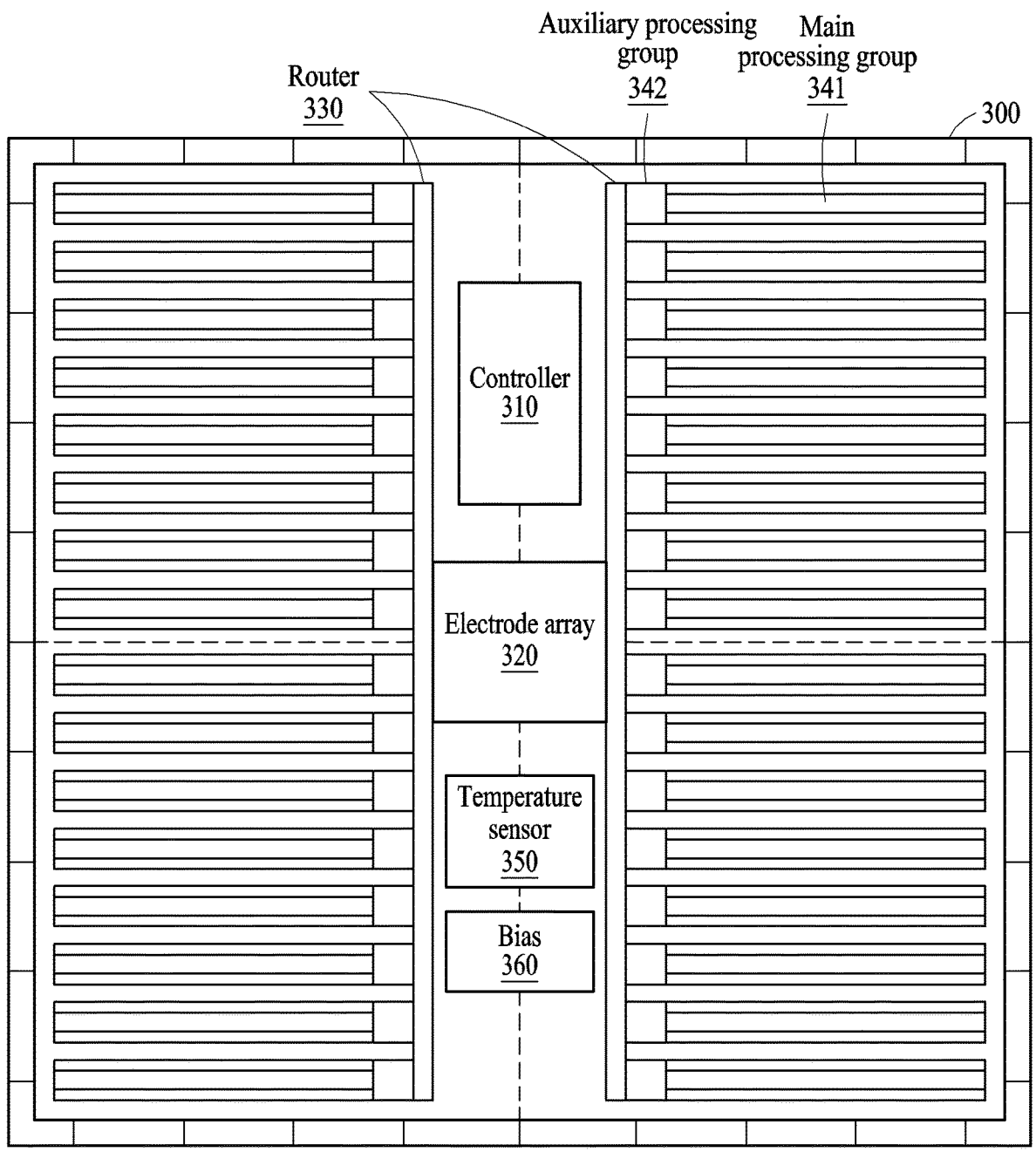
FIG. 3 illustrates an example structure of an example measuring apparatus implemented by a chip, in accordance with one or more embodiments.

FIG. 3 is a diagram illustrating an example structure an example measuring apparatus implemented by a chip, in accordance with one or more embodiments.

Referring to FIG. 3, an example measuring apparatus 300 may include a controller 310, an electrode array 320, a router 330, main processing groups, such as a main processing group 341, auxiliary processing groups, such as an auxiliary processing group 342, a temperature sensor 350, and a bias circuit 360. The controller 310 may correspond to a main controller. The controller 310 may be configured to control and calibrate an overall measurement operation. For example, the controller 310 may perform a command to run a test to each channel, may perform a command channel exchange based on a test result, may collect an output signal of each channel, and may generate a final output signal. The router 330 may be configured to perform communication by transmitting an input signal, transmitting an output signal, and based on a command. The temperature sensor 350 may be configured to sense a temperature from an input signal and the bias circuit 360 may be configured to control a bias of an analog signal. The structure illustrated in FIG. 3 is merely an example, and the measuring apparatus 300 may be implemented in a chip having a different structure from FIG. 3.

Figure 4:
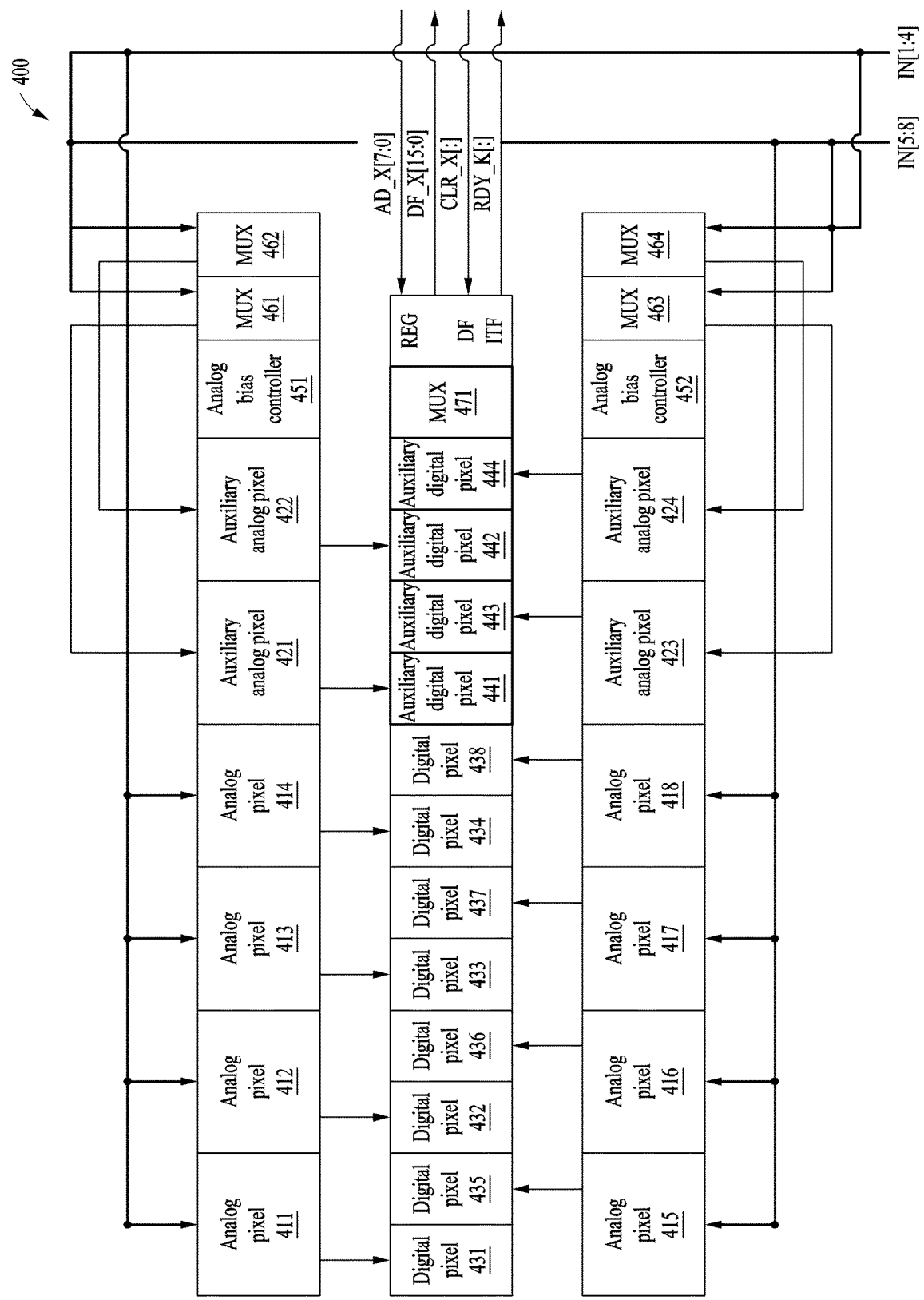
FIG. 4 illustrates an example structure of a circuit of a single slot, in accordance with one or more embodiments.

FIG. 4 is a diagram illustrating an example structure of a circuit of a single slot, in accordance with one or more embodiments. Referring to FIG. 4, a slot 400 may include analog pixels 411 to 418, auxiliary analog pixels 421 to 424, digital pixels 431 to 438, auxiliary digital pixels 441 to 444, analog bias controllers 451 and 452, MUXs 461 to 464 and 471, a register (REG), a digital filter (DF), and an interface (ITF). Although FIG. 4 illustrates an example that the slot 400 includes 8 main channels and 4 auxiliary channels, this is only an example, and the number of main channels and/or auxiliary channels may vary.

Corresponding pairs of the analog pixels 411 to 418 and the digital pixels 431 to 438 may correspond to the main signal processors and/or the main channels. The corresponding pairs of the auxiliary analog pixels 421 to 424 and the auxiliary digital pixels 441 to 444 may correspond to the auxiliary signal processors and/or the auxiliary channels. Each of the analog pixels 411 to 418 and the auxiliary analog pixels 421 to 424 may include at least one of an ADC, a signal generator (e.g., a current generator and a voltage generator), and an amplifier. Each of the digital pixels 431 to 438 and the auxiliary digital pixels 441 to 444 may include at least one of a controller and a clock generator.

When at least some of the main signal processors and/or the main channels satisfy a replacement condition, the at least some of the main signal processors and/or the main channels may be replaced by the auxiliary signal processors and/or the auxiliary channels. For channel exchange, the MUXs 461 to 464 may provide an input signal IN of a replacement target to at least some of the auxiliary signal processors and/or the auxiliary channels.

The main controller may transmit a request signal AD_X to the slot 400 by specifying a specific channel. The MUX 471 may select an output signal DF_X of the specific channel based on the request signal AD_X from among output signals of a plurality of channels. The main controller may notify with a clear signal CLR_X whether the output signal DF_X is received. A ready signal RDY_K may be used to determine whether the main controller is able to receive the output signal DF_X. The input signal IN may be provided to the analog pixels 411 to 418 and the MUXs 461 to 464 from an electrode array.

Figure 5:
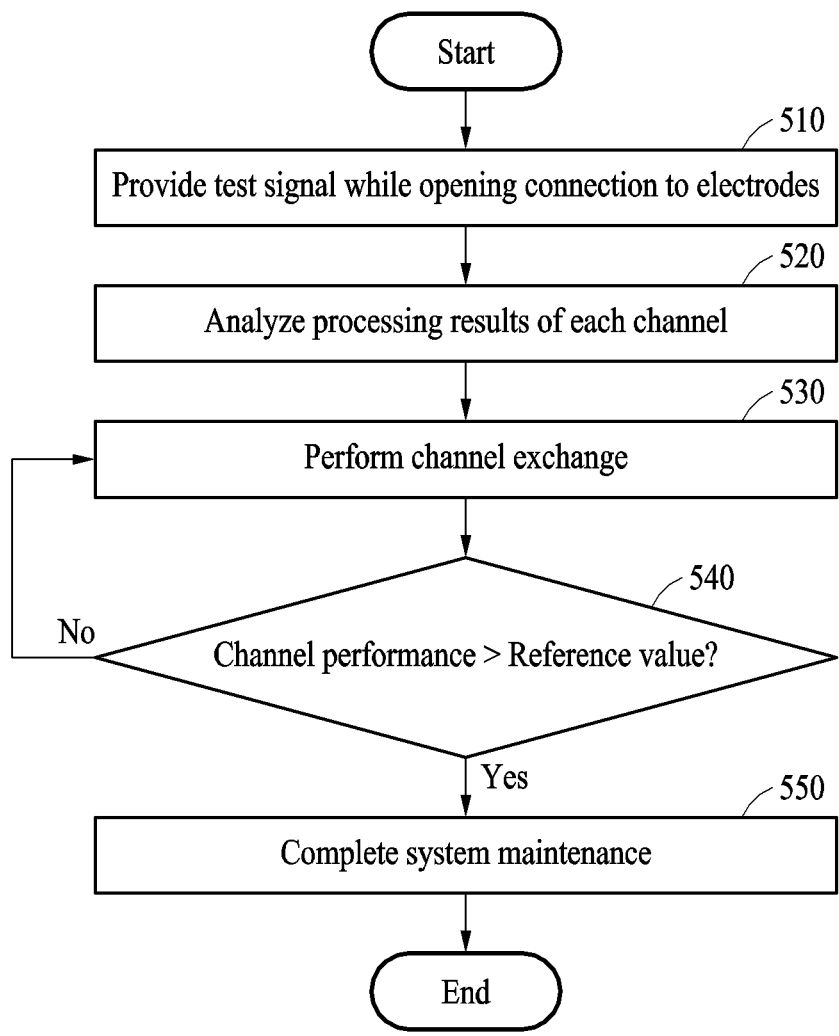
FIG. 5 is a flowchart illustrating an example test operation, in accordance with one or more embodiments.

FIG. 5 is a flowchart illustrating an example test operation, in accordance with one or more embodiments. One or more blocks of FIG. 5, and combinations of the blocks, can be implemented by special purpose hardware-based computer that perform the specified functions, or special purpose hardware configured by execution of computer instructions by one or more processors. In addition to the description of FIG. 5 below, the descriptions of FIGS. 1-4 are also applicable to FIG. 5, and are incorporated herein by reference. Thus, the above description may not be repeated here.

Referring to FIG. 5, in operation 510, a test signal may be provided while a connection to electrodes is open. Since an external input signal may enters through the electrodes, as the connection to the electrodes opens, an independent test for each channel may be performed while an external connection is blocked. The test signal may have a known waveform (e.g., a triangular waveform, a sine waveform, and the like). Each channel may correspond to each main signal processor and/or each auxiliary signal processor.

In operation 520, a processing result of each channel may be analyzed. A result signal of each channel may be determined as the test signal passes through each channel. The processing result may be determined based on a difference between the test signal and the result signal. When there is a channel with a large difference, the channel may be determined to be defective. A defect may be determined, as only examples, to be an error or performance degradation based on the level of the difference. It may be determined that the defective channel satisfies a replacement condition.

In operation 530, channel exchange may be performed. The defective channel may be replaced with a different channel, for example, an auxiliary channel. For example, when a main channel of a main signal processor is defective, the main channel may be replaced by an auxiliary channel of an auxiliary signal processor. When replacement targets satisfying the replacement condition are detected from the main signal processors, a replacement priority of the replacement targets may be determined based on the level of defects of the replacement targets, and the auxiliary signal processors may be applied in order from a highest priority to a lowest priority. For example, an error channel may have a higher priority than a performance degraded channel.

In operation 540, the channel performance may be compared to a reference value and operation 530 may be repeated until the channel performance exceeds the reference value. Channel exchange for various channels during iterations may be performed. When the channel performance exceeds the reference value, in operation 550, system maintenance may be completed.

An execution time of operations 510 to 550 may include at least one of a time point of initial booting of the system, a time point based on a preset period, and a time point based on an aperiodic request. Operations 510 to 550 may be performed by a configuration of each channel under control by the main controller of the measuring apparatus.

Figure 6:
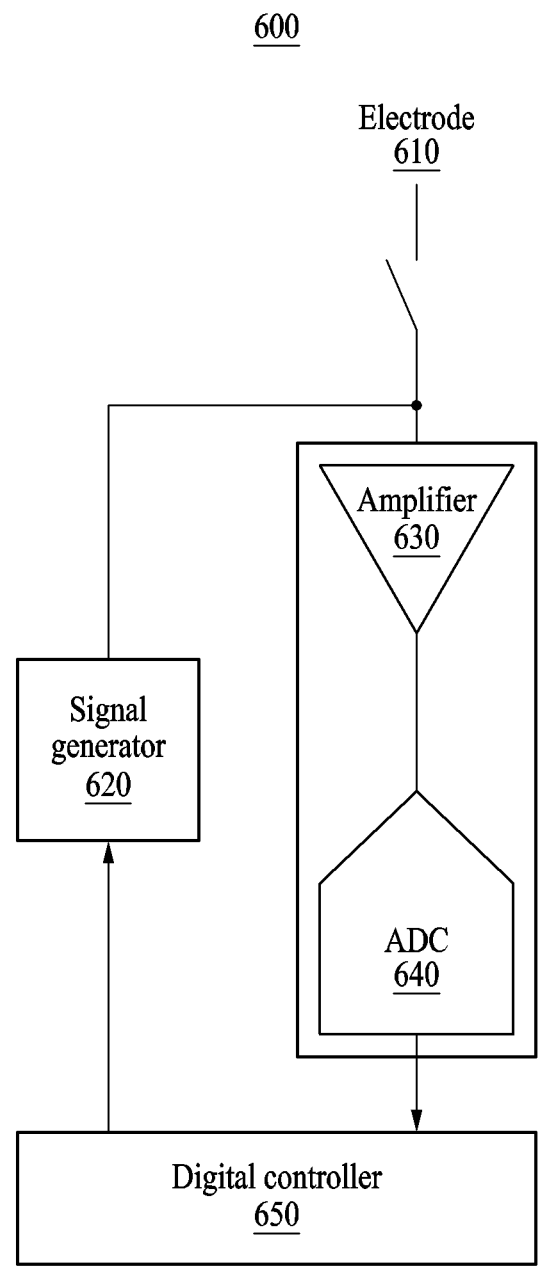
FIG. 6 illustrates an example structure of a test circuit configured to perform a test operation, in accordance with one or more embodiments.

FIG. 6 is a block diagram illustrating an example structure of a test circuit configured to perform a test operation, in accordance with one or more embodiments.

Referring to FIG. 6, a test circuit 600 may include a digital controller 650, a signal generator 620, an amplifier 630, and an ADC 640. The test circuit 600 may correspond to at least a portion of each channel. At least a portion (e.g., the amplifier 630 and the ADC 640) of the test circuit 600 may correspond to at least a portion of a main signal processor and/or an auxiliary signal processor.

The signal generator 620 may generate a test signal based on control of the digital controller 650, and the test signal may be provided to a channel while an electrode 610 is blocked from the channel. The channel may include the amplifier 630 and/or the ADC 640. As the test signal passes through a channel, a result signal may be determined. The digital controller 650 may perform channel exchange based on the result signal.

FIG. 7 is a diagram illustrating an example relationship between components in a structure in which auxiliary signal processors are shared, in accordance with one or more embodiments.

FIG. 7 illustrates a connection relationship between an electrode array EA, an input signal IN, auxiliary (or sub) AFEs S-AFE 1 to S-AFE 12, and main AFE groups AFE 1 to AFE 8. An AFE may correspond to a main processing group and S-AFE may correspond to an auxiliary signal processor. For ease of description, each auxiliary signal processor is displayed by being merged with a corresponding MUX.

Each main AFE group may include a first number of main signal processors and a third number of main AFE groups may share one auxiliary signal processor, where the first number and the third number are predetermined. FIG. 7 illustrates an example that the first number is 8 and the third number is 4. In this example, main AFE groups that are close to each other (e.g., neighboring main AFE groups) among the main AFE groups, may share auxiliary signal processors. For example, the main AFE groups AFE 1 to AFE 4 may share the auxiliary AFE S-AFE 5.

The auxiliary AFEs may be distributed to the main AFE groups in a predetermined pattern. The main AFE groups, the auxiliary AFE, and the third number may be defined by AFE i, S-AFE j, and k, respectively. In this example, S-AFE i+1, i+2, . . . , i+k may be allocated to AFE i. For example, when k is 4 as illustrated in FIG. 7, S-AFE 2, 3, 4, and 5 may be allocated to AFE 1 and S-AFE 3, 4, 5, and 6 may be allocated to AFE 2.

Referring to FIG. 7, [c1:c2] may specify channels of c1 to c2. For example, the main AFE group AFE 1 may include 8 main signal processors and may receive input signals IN[32:39] of the 32th channel to the 39th channel. The main AFE groups AFE 1 to AFE 4 may be allocated to the auxiliary AFE S-AFE 5, and thus, the auxiliary AFE S-AFE 5 and the corresponding MUX may cover input signals IN[32:63].

FIG. 8 is a flowchart illustrating an example of an optimization operation of channel exchange, in accordance with one or more embodiments. One or more blocks of FIG. 8, and combinations of the blocks, can be implemented by special purpose hardware-based computer that perform the specified functions, or special purpose hardware configured by execution of computer instructions by one or more processors. In addition to the description of FIG. 8 below, the descriptions of FIGS. 1-7 are also applicable to FIG. 8, and are incorporated herein by reference. Thus, the above description may not be repeated herein. When defects simultaneously occur in different slots that share a predetermined auxiliary signal processor, a problem that which main processing group uses the auxiliary signal processor may occur. FIG. 8 may provide a method of optimizing allocation of auxiliary signal processors. According to one embodiment, operations 801 to 809 may be performed as operation 530 of FIG. 5.

Referring to FIG. 8, in operation 801, a measuring apparatus may determine a slot with the highest level of a defect. The defect may include an error and performance degradation. A defect level may be determined based on the number of error channels in each slot. When the number of error channels is the same, the defect level of each slot may be determined by additionally considering the number of performance degraded channels. A slot with the highest defect level may be referred to as a defective slot.

In operation 802, the measuring apparatus may determine a slot with the lowest defect level among neighboring slots of the defective slot. A neighboring slot may refer to a slot arranged adjacent to a defective slot or a slot that shares an auxiliary signal processor with the defective slot. When there are many channels that may have to be exchanged in the defective slot, a plurality of neighboring slots may be selected. For example, when a defective slot performs channel exchange through a sub channel that is shared with a first neighboring slot and a second neighboring slot, and the first neighboring slot has a defect and the second neighboring slot does not have a defect, the defective slot may perform channel exchange through the sub channel shared with the second neighboring slot.

In operation 803, the measuring apparatus may determine whether the error and performance degradation are correctable. The measuring apparatus may determine whether there are sufficient auxiliary signal processors to correct errors and performance degradation of the defective slot and the neighboring slots by considering conditions of the neighboring slots.

In operation 804, the measuring apparatus may determine to use the sub channel of the neighboring slot as much as possible, in operation 805, the measuring apparatus may correct errors of the defective slot and the neighboring slot, and in operation 806, the measuring apparatus may correct performance degradation of the neighboring slot and the defective slot. Error correction may take precedence over defective slot correction.

When correction of both errors and performance degradation is determined to be difficult in operation 803, operation 807 may be performed. In operation 807, the measuring apparatus may determine whether error correction of the neighboring slot is available. In operation 808, the measuring apparatus may determine whether to use the sub channel of the neighboring slot as much as possible. In operation 809, the measuring apparatus may correct errors of the defective slot and the neighboring slot.

Figure 9:
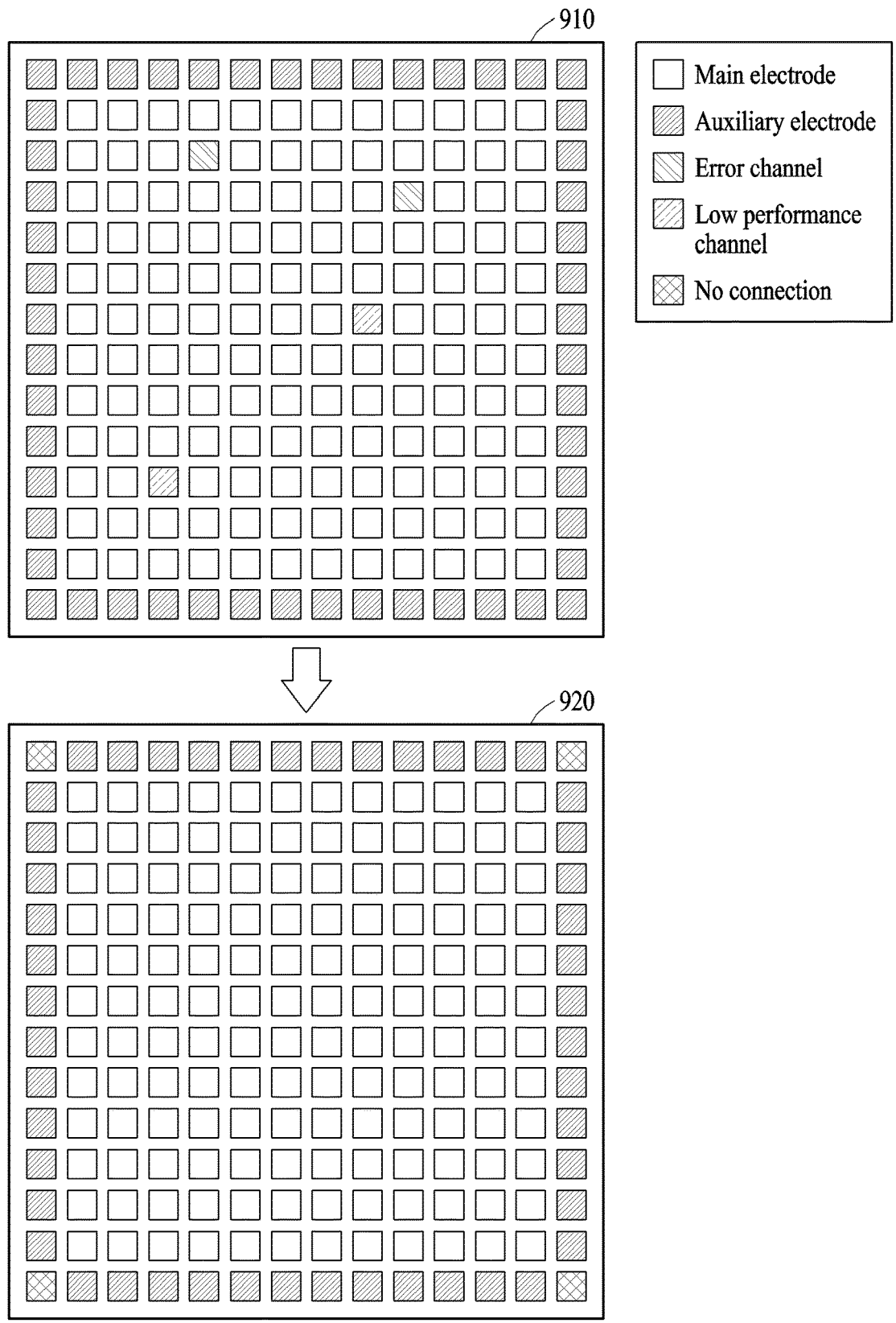
FIG. 9 illustrates an example operation of an electrode array including a main electrode and an auxiliary electrode, in accordance with one or more embodiments.

FIG. 9 is a diagram illustrating an example operation of an electrode array including a main electrode and an auxiliary electrode, in accordance with one or more embodiments.

Referring to FIG. 9, an electrode array may be controlled to switch from a first operation state 910 to a second operation state 920 based on a channel exchange operation. The electrode array may include main electrodes and auxiliary electrodes. The main electrodes may be arranged in the central area of the electrode array compared to the auxiliary electrodes. The electrode array may measure input signals by using the main electrodes and the auxiliary electrodes. According to an example of FIG. 9, even if channel exchange of a main channel is not necessary, the auxiliary channel may operate as an independent measuring channel.

In the first operation state 910 of the electrode array, an error channel and a performance degraded channel (hereinafter, referred to as a low performance channel) among the main electrodes may be detected. The main electrodes may correspond to main channels and may be connected to main signal processors. The auxiliary electrodes may correspond to auxiliary channels and may be connected to auxiliary signal processors. In the second operation state 920, channel exchange for the main electrode of the error channel and the low performance channel may be performed. Based on channel exchange, an auxiliary channel of the auxiliary electrode may be applied to the main electrode of the error channel and the low performance channel. The previous auxiliary electrode to which the auxiliary channel used for channel exchange is connected may be in a connection lost state. For example, a first main signal processor may be connected to a first main electrode among the main electrodes and a first auxiliary signal processor may be connected to a first auxiliary electrode among the auxiliary electrodes. As the first main signal processor satisfies a replacement condition, the first auxiliary signal processor may replace the first main signal processor and may be connected to the first main electrode.

Figure 10:
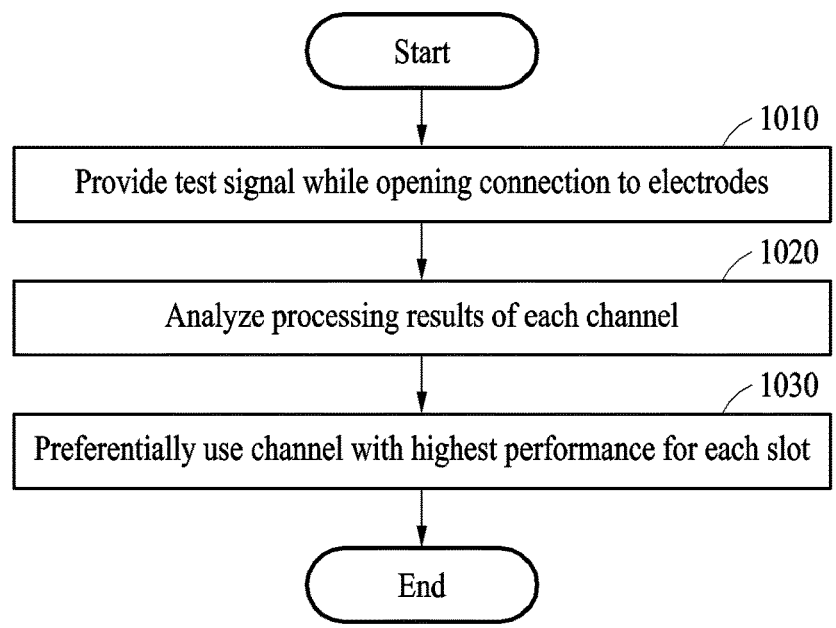
FIG. 10 is a flowchart illustrating an example of deriving the maximum performance by implementing auxiliary signal processors, in accordance with one or more embodiments.

FIG. 10 is a flowchart illustrating an example of deriving the maximum performance by implementing auxiliary signal processors, in accordance with one or more embodiments. One or more blocks of FIG. 10, and combinations of the blocks, can be implemented by special purpose hardware-based computer that perform the specified functions, or special purpose hardware configured by execution of computer instructions by one or more processors. In addition to the description of FIG. 10 below, the descriptions of FIGS. 1-9 are also applicable to FIG. 10, and are incorporated herein by reference. Thus, the above description may not be repeated herein.

Referring to FIG. 10, each auxiliary signal processor may be in a state where they are selectively connectable to all electrodes in a slot through a corresponding MUX. In this example, main signal processors in the slot and the auxiliary signal processors may compete with each other to connect to an electrode, and a main signal processor or an auxiliary signal processor with the highest performance for the electrode may be connected to the electrode. For example, when a slot includes first main signal processors selectively connected to each electrode of a first electrode group among electrodes in an electrode array, and first auxiliary signal processors selectively connected to each electrode of the first electrode group, some of the first main signal processors and the first auxiliary signal processors selected in order of high performance may be applied to the first electrode group.

Referring to FIG. 10, in operation 1010, a test signal may be provided while connection to electrodes is open and in operation 1020, a processing result of each channel may be analyzed. The descriptions provided with reference to FIGS. 5 and 6 may apply to operations 1010 and 1020. In operation 1030, a channel with the highest performance for each slot may be preferentially used. In an electrode of a slot, when a main channel shows higher performance than an auxiliary channel, a measurement operation may be performed through a main signal processor of the main channel and in another electrode, when an auxiliary channel shows higher performance than a main channel, a measurement operation may be performed through an auxiliary signal processor of the auxiliary channel. According to an example of FIG. 10, the best performance of each slot may be derived through an auxiliary channel.

Figure 11:
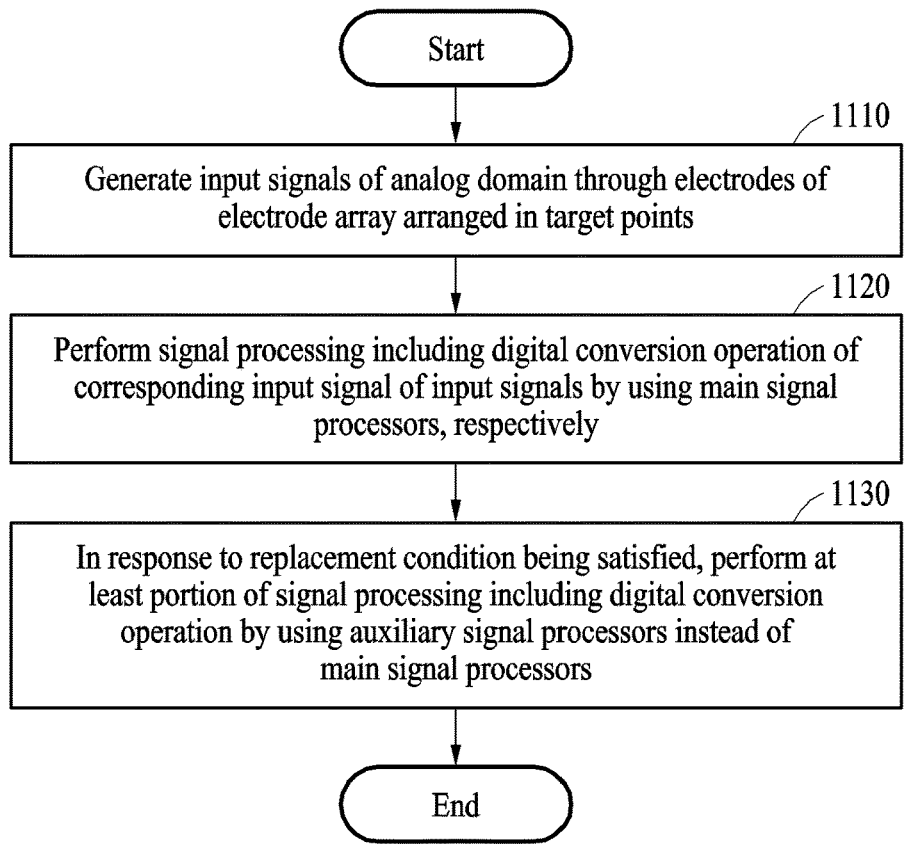
FIG. 11 is a flowchart illustrating an example measuring method implementing an example electrode array, in accordance with one or more embodiments.

FIG. 11 is a flowchart illustrating an example of a measuring method using an electrode array, in accordance with one or more embodiments. One or more blocks of FIG. 11, and combinations of the blocks, can be implemented by special purpose hardware-based computer that perform the specified functions, or special purpose hardware configured by execution of computer instructions by one or more processors. In addition to the description of FIG. 11 below, the descriptions of FIGS. 1-10 are also applicable to FIG. 11, and are incorporated herein by reference. Thus, the above description may not be repeated herein.

Referring to FIG. 11, in operation 1110, a measuring apparatus may measure input signals of an analog domain through electrodes of an electrode array arranged at target points. In operation 1120, the measuring apparatus may perform signal processing including digital conversion of corresponding input signals of the input signals by using main signal processors, respectively, and in operation 1130, in response to a replacement condition being satisfied, the measuring apparatus may perform at least a portion of signal processing including digital conversion by implementing auxiliary signal processors instead of the main signal processors.

Operation 1130 may include an operation that implements the auxiliary signal processors instead of the main signal processors by using MUXs that selectively connect candidate electrodes of the electrodes to corresponding auxiliary signal processors of the auxiliary signal processors.

The main signal processors may be divided into a predetermined first number and may configure a plurality of slots, and the auxiliary signal processors may be divided into a predetermined second number and may be dedicatedly allocated to each of the plurality of slots.

In a non-limiting example, the electrode array may be a multi-channel MEA.

Additionally, the descriptions provided with reference to FIGS. 1 to 10 and FIG. 12 may apply to the measuring method of FIG. 11.

Figure 12:
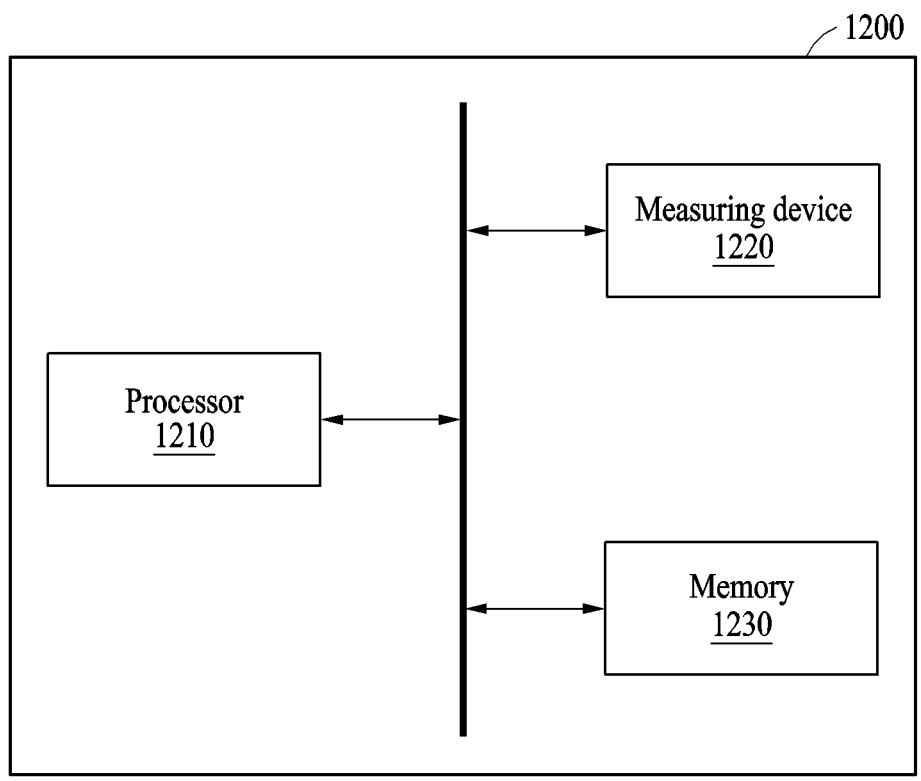
FIG. 12 illustrates an example configuration of an example bioreaction recording apparatus, in accordance with one or more embodiments.

FIG. 12 is a block diagram illustrating an example of a configuration of an example apparatus, e.g., as or including, a bioreaction recording apparatus, in accordance with one or more embodiments.

Referring to FIG. 12, a bioreaction recording apparatus 1200 may include one or more processors 1210, a measuring device 1220, and a memory 1230. The memory 1230 may be connected to the one or more processors 1210 and the measuring device 1220, and may store instructions executable by the one or more processors 1210, data to be computed by the one or more processors 1210, or data processed by the one or more processors 1210. The memory 1230 may include a non-transitory computer-readable medium, for example, high-speed random-access memory (RAM), and/or a nonvolatile computer-readable storage medium (e.g., one or more disk storage devices, flash memory devices, or other nonvolatile solid state memory devices). The measuring device 1220 may measure a bioreaction and the memory 1230 may store the measured bioreaction. The one or more processors 1210 may control the measuring device 1220 and the memory 1230.

The measuring device 1220 may correspond to a measuring apparatus. The measuring device 1220 may perform the operations of FIGS. 1 to 11. For example, the measuring device 1220 may include an electrode array configured to measure input signals of an analog domain through electrodes arranged in a target point, main signal processors configured to perform signal processing including a digital conversion operation of corresponding input signals of the input signals, respectively, and in response to a replacement condition being satisfied, auxiliary signal processors configured to replace the main signal processors and perform at least some of the signal processing comprising the digital conversion operation.

The memory 1230 may store response data output by at least some of the main signal processors and the auxiliary signal processors.

The measuring device 1220 may further include MUXs that selectively connect candidate electrodes of the electrodes to corresponding auxiliary signal processors of the auxiliary signal processors.

The main signal processors may include a first main signal processor connected to a first electrode of the electrodes, the MUXs may include a first MUX configured to selectively connect a first auxiliary signal processor of the auxiliary signal processors to first candidate electrodes including the first electrode, and in response to the replacement condition being satisfied by the first main signal processor, the first MUX may connect the first electrode to the first auxiliary signal processor.

The main signal processors may be divided into a predetermined first number, and may configure a plurality of slots, and the auxiliary signal processors may be divided into a predetermined second number, and may be dedicatedly allocated to each of the plurality of slots.

The main signal processors may be divided into a predetermined first number and may configure a plurality of slots, and the auxiliary signal processors may be allocated to the plurality of slots such that a predetermined third number of slots of the plurality of slots share at least a portion of the auxiliary signal processors.

The measuring device 1220 may further include a controller configured to determine whether the main signal processors satisfy the replacement condition based on a performance test of the main signal processors.

The controller may be configured to, while connection between the electrodes and the main signal processors is open, provide a test signal to each of the main signal processors, analyze a processing result of each of the main signal processors in response to the test signal, and determine whether the main signal processors satisfy the replacement condition.

The controller may be configured to, when a plurality of replacement targets satisfying the replacement condition is detected from the main signal processors, determine a replacement priority of the replacement targets based on a defect level of the replacement targets and apply the auxiliary signal processor in order from a highest priority down.to a lowest priority The electrodes may include main electrodes connected to the main signal processors, and auxiliary electrodes connected to the auxiliary signal processors, and the electrode array may be configured to measure the input signals using the main electrodes and the auxiliary electrodes.

The main signal processors may include a first main signal processor connected to a first main electrode among the main electrodes, the auxiliary signal processors may include a first auxiliary signal processor connected to a first auxiliary electrode among the auxiliary electrodes, and in response to the replacement condition being satisfied by the first main signal processor, the first auxiliary signal processor may replace the first main signal processor, and may be connected to the first main electrode.

The main electrodes may be arranged in a central area of the electrode array compared to the auxiliary electrodes, and in response to the replacement condition being satisfied by the first main signal processor, data measurement through the first auxiliary electrode may be paused.

The main signal processors may include first main signal processors selectively connected to each electrode of a first electrode group among the electrodes, the auxiliary signal processors may include first auxiliary signal processors selectively connected to each electrode of the first electrode group, and some of the first main signal processors and the first auxiliary signal processors selected in order from high performance may be applied to the first electrode group.

In an example, the electrode array may be a multi-channel MEA.

Additionally, the descriptions provided with reference to FIGS. 1 to 11 may apply to the bioreaction recording apparatus 1200.

The main signal processors 120, auxiliary signal processors 130, MUX 140, controller 310, temperature sensor 350, signal generator 620, amplifier 630, ADC 640, digital controller 650, one or more processors 1210, measuring device 1220, memory 1230, and other devices, and other components described herein are implemented as, and by, hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods that perform the operations described in this application, and illustrated in FIGS. 1-12, are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller, e.g., as respective operations of processor implemented methods. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that be performed by the hardware components and the methods as described above. In one example, the instructions or software include machine code that is directly executed by the one or more processors or computers, such as machine code produced by a compiler. In another example, the instructions or software include higher-level code that is executed by the one or more processors or computers using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), EEPROM, RAM, DRAM, SRAM, flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors and computers so that the one or more processors and computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent to one of ordinary skill in the art, after an understanding of the disclosure of this application, that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

What is claimed is:

1. An apparatus, comprising:
   an electrode array configured to measure input signals of an analog domain through electrodes arranged in a target point;
   main signal processors configured to perform signal processing operations on corresponding respective input signals of the input signals;
   auxiliary signal processors configured to replace at least one of the main signal processors, and perform at least some of the signal processing operations in response to a replacement condition being satisfied, and
   a controller configured to, when a plurality of replacement targets satisfying the replacement condition is detected from the main signal processors, determine a replacement priority of the replacement targets based on a defect level of the replacement targets.

2. The apparatus of claim 1, wherein the signal processing operations comprise at least one of a digital conversion operation, a signal generation operation, a signal amplification operation, a control operation, and a clock generation operation.

3. The apparatus of claim 2, wherein each of the main signal processors comprise an analog digital converter (ADC) configured to perform the digital conversion operation.

4. The apparatus of claim 1, further comprising:
   multiplexers (MUXs) configured to selectively connect candidate electrodes of the electrodes to corresponding auxiliary signal processors of the auxiliary signal processors.

5. The apparatus of claim 4, wherein the main signal processors comprise a first main signal processor connected to a first electrode of the electrodes,
   the MUXs comprise a first MUX configured to selectively connect a first auxiliary signal processor of the auxiliary signal processors to first candidate electrodes comprising the first electrode, and
   the first MUX is configured to connect the first electrode to the first auxiliary signal processor in response to the replacement condition being satisfied by the first main signal processor.

6. The apparatus of claim 1, wherein the main signal processors are connected to the respective electrodes before the replacement condition is satisfied.

7. The apparatus of claim 1, wherein the main signal processors are divided into a predetermined first number of main signal processors, and configure a plurality of slots, and
   the auxiliary signal processors are divided into a predetermined second number of auxiliary signal processors, and are dedicatedly allocated to each of the plurality of slots.

8. The apparatus of claim 1, wherein the main signal processors are divided into a predetermined first number, and configure a plurality of slots, and
   the auxiliary signal processors are allocated to the plurality of slots such that a predetermined third number of slots of the plurality of slots share at least a portion of the auxiliary signal processors.

9. The apparatus of claim 1, wherein the controller is configured to determine whether the main signal processors satisfy the replacement condition based on a performance test of the main signal processors.

10. The apparatus of claim 9, wherein the controller is configured to, while connection between the electrodes and the main signal processors is open, provide a test signal to each of the main signal processors, analyze a processing result of each of the main signal processors in response to the test signal, and determine whether the main signal processors satisfy the replacement condition.

11. The apparatus of claim 9, wherein the controller is configured to apply the auxiliary signal processor in an order from a highest priority to a lowest priority, associated with the replacement priority of the replacement targets.

12. The apparatus of claim 1, wherein the electrodes comprise main electrodes connected to the main signal processors and auxiliary electrodes connected to the auxiliary signal processors, and
the electrode array is configured to measure the input signals by implementing the main electrodes and the auxiliary electrodes.

13. The apparatus of claim 12, wherein the main signal processors comprise a first main signal processor connected to a first main electrode among the main electrodes,
the auxiliary signal processors comprise a first auxiliary signal processor connected to a first auxiliary electrode among the auxiliary electrodes, and
the first auxiliary signal processor is configured to replace the first main signal processor and connect to the first main electrode in response to the replacement condition being satisfied by the first main signal processor.

14. The apparatus of claim 13, wherein the main electrodes are arranged in a central area of the electrode array compared to the auxiliary electrodes, and
data measurement through the first auxiliary electrode is paused in response to the replacement condition being satisfied by the first main signal processor.

15. The apparatus of claim 1, wherein the main signal processors comprise first main signal processors selectively connected to each electrode of a first electrode group among the electrodes,
the auxiliary signal processors comprise first auxiliary signal processors selectively connected to each electrode of the first electrode group, and
some of the first main signal processors and the first auxiliary signal processors selected in order from a high performance level to a low performance level are applied to the first electrode group.

16. The apparatus of claim 1, wherein the electrode array comprises a multi-channel microelectrode array (MEA).

17. A method comprising:
measuring input signals of an analog domain through electrodes of an electrode array arranged in a target point;
performing signal processing operations on corresponding respective input signals of the input signals by implementing respective main signal processors; and
performing at least some of the signal processing operations by implementing auxiliary signal processors instead of the main signal processors in response to a replacement condition being satisfied, including, when a plurality of replacement targets satisfying the replacement condition is detected from the main signal processors, determining a replacement priority of the replacement targets based on a defect level of the replacement targets.

18. The method of claim 17, wherein the signal processing operations comprise at least one of a digital conversion operation, a signal generation operation, a signal amplification operation, a control operation, and a clock generation operation.

19. The method of claim 18, wherein the performing of the at least some of the signal processing operations by implementing the auxiliary signal processors comprises:
implementing the auxiliary signal processors instead of the main signal processors with multiplexers (MUXs) that are configured to selectively connect candidate electrodes of the electrodes to corresponding auxiliary signal processors of the auxiliary signal processors.

20. An apparatus, comprising:
an electrode array comprising a plurality of electrodes disposed on target points;
analog to digital converters (ADC) configured to perform respective digital conversion operations on input signals of respective signal transmission channels;
respective auxiliary signal processors configured to perform one or more channel exchanges to replace a corresponding one or more of respective digital conversion operations of one or more of the ADCs based on a determination of a defect in the one or more ADCs;
a multiplexer (MUX) configured to selectively perform connection operations between one or more electrodes of the electrode array and a corresponding one or more of the auxiliary signal processors of the respective auxiliary signal processors; and
a controller configured to, when a plurality of replacement targets satisfying the replacement condition is detected from the one or more ADCs, determine a replacement priority of the replacement targets based on a defect level of the replacement targets.

* * * * *